United States Patent [19]

Brown et al.

[11] 4,147,735

[45] Apr. 3, 1979

[54] SEPARATION OF ORGANIC COMPOUNDS FROM MIXTURES BY CLATHRATION

[75] Inventors: Douglas H. Brown; Ronald J. Cross; David D. MacNicol, all of Glasgow, Scotland

[73] Assignee: National Research Development Corporation, London, England

[21] Appl. No.: 892,077

[22] Filed: Mar. 31, 1978

[30] Foreign Application Priority Data

Apr. 13, 1977 [GB] United Kingdom ............. 15242/77
Aug. 5, 1977 [GB] United Kingdom ............. 32963/77
Sep. 6, 1977 [GB] United Kingdom ............. 37169/77

[51] Int. Cl.² .............................................. C07C 7/00
[52] U.S. Cl. .............................................. 260/674 WC
[58] Field of Search .................. 260/674 WC, 674 R

[56] References Cited

U.S. PATENT DOCUMENTS

2,926,206  2/1960  Schaeffer et al. ............ 260/674 WC
3,426,068  2/1969  Coscia ......................... 260/674 WC

FOREIGN PATENT DOCUMENTS

872819  11/1959  United Kingdom ............ 260/674 WC

OTHER PUBLICATIONS

"Clathration of Hard-To-Separate Aromatic Mixtures with New Werner Complexes" by Radzitsky et al., I&EC Process Design and Development, vol. 1, No. 1 (Jan. 1962), pp. 10–14.

Primary Examiner—O. R. Vertiz
Assistant Examiner—Wayne A. Langel
Attorney, Agent, or Firm—Jacobs & Jacobs

[57] ABSTRACT

A method for the separation of organic compounds by clathration in which there is used as a host a compound of formula I:

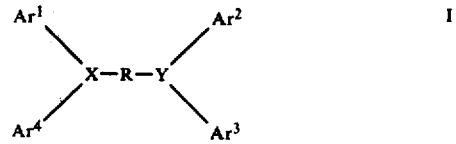

wherein: $Ar^1$ $Ar^2$ and $Ar^3$ and $Ar^4$, which may be identical or different, represent aromatic groups; X and Y, which may be identical or different, represent P, As or Sb or P, As or Sb to which O, S or Se are bound; R represents a bond joining X and Y, a substituted or unsubstituted alkylene group, a substituted or unsubstituted arylene group, a substituted or unsubstituted alkenylene group or a substituted or unsubstituted alkynylene group. The compound of formula I in which $Ar^1$-$Ar^4$ represent phenyl, X and Y each represent P=Se and R represents $-(CH_2)_2-$ is particularly useful for the clathration of p-xylene.

14 Claims, No Drawings

SEPARATION OF ORGANIC COMPOUNDS FROM MIXTURES BY CLATHRATION

This invention relates to the separation of organic compounds from mixtures by clathration.

At present xylene isomers are separated one from another by clathration using as hosts for example, Werner complexes such as $Ni(SCN)_2 \cdot 4(\alpha\text{-phenylethylamine})$ or phosphonitrile derivatives such as p,p-(o-phenylenedioxy)-phosphonitrile trimer.

Host compounds have now been found which by clathration can effect the separation of various organic compounds, including the separation of p-xylene from mixtures thereof with other isomers, the degree of separation being relatively increased.

Accordingly, the present invention comprises a method for the separation of organic compounds by clathration in which there is used as a host a compound of formula I:

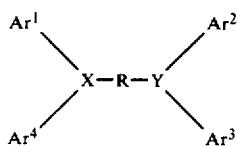

wherein: $Ar^1$ $Ar^2$ and $Ar^3$ $Ar^4$, which may be identical or different, represent aromatic groups; X and Y, which may be identical or different, represent P, As or Sb or P, As or Sb to which O, S or Se are bound;

R represents a bond joining X and Y, a substituted or unsubstituted alkylene group, a substituted or unsubstituted arylene group, a substituted or unsubstituted alkenylene group or a substituted or unsubstituted alkynylene group.

Certain compounds of Formula I are described in "Organic Phosphorus Compounds" Editors: Kosolapoff and Maier; John Wylie and Sons, New York, 1972: Vol 1 pp 1–287 (tertiary phosphines), Vol 3 pp 341–500 (phosphine oxides) and Vol 4 pp 1–73 (phosphine sulphides, selenides and tellurides). The compound (I) in which $Ar^1$ to $Ar^4$=Ph, X and Y=P=Se and R=—$(CH_2)_2$—, which is of particular interest, is disclosed by Philip Nicpon and Devon W. Meek in Inorganic Chemistry, 5 (7), 1297 (1966) and may be prepared by the method described therein.

The present invention comprises in a further aspect those compounds of Formula I which are novel.

In host compounds of particular interest, $Ar^1$–$Ar^4$ represent substituted or unsubstituted aryl groups e.g. phenyl groups.

R moreover preferably represents an alkylene group, —$(CH_2)_n$— wherein n is preferably 1–3 and X,Y which are preferably identical represent the group P=Se or P=S in preferred compounds.

The present invention finds particular application in the separation of hydrocarbons from one another and from other compounds.

Accordingly, the present invention further comprises a method for the separation by clathration of a hydrocarbon from a mixture comprising the hydrocarbon, in which the mixture is treated with a host compound of Formula I so that said hydrocarbon forms an adduct with the host compound. In general the hydrocarbon is subsequently recovered from the adduct although the process may, if desired, be applied to the removal of an unwanted component of a mixture therefrom.

The present process is applicable to the separation by clathration of aromatic hydrocarbons, notably mononuclear aromatic hydrocarbons and is of particular interest for the separation of isomers of the following compounds from one another and, if desired, from other compounds: xylenes, ethyltoluenes, cymenes, diethylbenzenes, chlorotoluenes, dichlorobenzenes, toluidines, nitrotoluenes, methylanisoles and cresols.

The process is particularly suitable for the separation of xylene isomers from one another by clathration of p-xylene and for the separation of xylene isomers and in particular p-xylene from ethylbenzene.

The present process of the present invention may be carried into effect by dissolving the compound of Formula I in the mixture, if necessary by either adding a solvent or raising the temperature of both. The mixture may then be cooled and, if desired, seeded to precipitate the adduct.

In order to simplify the separative procedure however it is generally preferable for the guest hydrocarbon to be absorbed by the host compound.

Accordingly the present invention comprises, in a further aspect, a method for the separation by clathration of a hydrocarbon from a mixture comprising the hydrocarbon, in which the mixture is treated with a host compound of formula I, said host compound and mixture being disposed in separate phases, so that said hydrocarbon forms an adduct with the host compound.

The host compound is generally present as a solid phase or a component thereof and the mixture preferably provides a liquid phase although if desired the mixture may be dissolved in a suitable solvent providing the liquid phase, the host compound being insoluble in said solvent. Absorption of the guest hydrocarbon from the vapour phase is however envisaged.

The host compound is preferably conditioned prior to use by formation of an adduct with the guest hydrocarbon which is to be separated from the mixture and subsequent removal of the guest hydrocarbon therefrom. In the conditioning step the adduct may be formed for example by precipitation from solution as hereinbefore described.

Recovery of the guest compound may be achieved, for example, by heating the adduct, if necessary at reduced pressure or, after separation of the adduct from the mixture, by dissolution thereof in a suitable solvent such as chloroform.

The present invention is illustrated by the following Examples:

EXAMPLE 1

(No co-solvent)

3 g of (I) [$Ar^1$ to $Ar^4$=Ph, X and Y represent P=Se, R=—$(CH_2)_2$—]were dissolved in 25 ml. of an equivolume mixture of o-xylene, m-xylene, p-xylene and ethylbenzene at 383° K. The solution was allowed to cool at approximately 0.5°–1.0°/min. Seeding with crystal fragments which contained p-xylene initiated crystallisation when the temperature was 360° K. 2.9 g of adduct (1)-p-xylene was isolated. The adduct was purified by decantation then evacuation at room temperature.

The separated hydrocarbon was recovered from the adduct by heating the adduct at reduced pressure.

The isolated hydrocarbon was analysed by i.r. absorption methods and shown to consist of 95.5% p- xylene, 2.5% ethylbenzene, 1.2% m-xylene and 0.8% o-xylene (all values subject to an error ±0.1%).

EXAMPLE 2

(With CHCl₃ as co-solvent)

2g of (I) [Ar¹ to Ar⁴=Ph, X and Y represent P=Se, R=—(CH₂)₂—] were dissolved in 25 ml. of an equivolume mixture of o-xylene, m-xylene, p-xylene, ethylbenzene and chloroform at 363° K. This solution was allowed to cool at approximately 0.5°–1.0°/min. No seeding was employed. 1.9 g of adduct (I) p-xylene was isolated.

This was purified by decantation and evacuation at room temperature to remove surface liquid.

The separated hydrocarbon was recovered from the clathrate inclusion compound as in Example 1 (see above). Analysis by ¹H n.m.r. spectroscopy indicated that the separated hydrocarbon consisted of p-xylene (95% or better) with trace quantities only of ethylbenzene, o-xylene, or m-xylene.

EXAMPLE 3

(Absorption Method)

1.90 g of (I) [Ar' - Ar"=Ph, X=Y=(P=Se), R=(CH₂)₂] was stirred for 20 h. under a nitrogen atmosphere in 8 ml of an equivolume mixture of o-xylene, m-xylene, p-xylene and ethylbenzene at 295° K. 1.85 g of adduct (I)-p-xylene was isolated after filtration, n-pentane washing, and evacuation at room temperature.

The separated hydrocarbon was recovered from the adduct by heating the adduct at reduced pressure.

The isolated hydrocarbon was analysed by i.r. absorption methods and shown to consist of 96.8% p-xylene, 2.0% ethylbenzene, 0.7% m-xylene, and 0.5% o-xylene (all values subject to an error =/±0.1%).

We claim:

1. In the method of separating organic compounds by clathration, the improvement which comprises using as a host a compound of the formula:

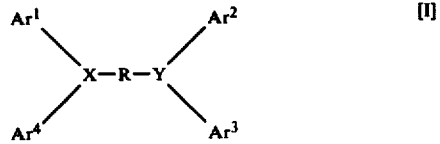

[I]

where
in each of Ar¹, and Ar², Ar³ and Ar⁴ is identical to or different from the others and is an aromatic group;
each of X and Y is identical to or different from the other and is P, As or Sb, or P, As or Sb to which O, S or Se is bound;
R is a bond joining X and Y, or substituted or unsubstituted alkylene, substituted or unsubstituted arylene, substituted or unsubstituted alkenylene or substituted or unsubstituted alkynylene.

2. In the method according to claim 1 for the separation by clathration of a hydrocarbon from a mixture comprising the hydrocarbon, the improvement which consists of treating said mixture with said host compound whereby said hydrocarbon forms an adduct with said host compound.

3. A method according to claim 2, in which the hydrocarbon which is separated by clathration is an aromatic hydrocarbon.

4. A method according to claim 3, in which the aromatic hydrocarbon is mononuclear.

5. A method according to claim 2, in which the hydrocarbon which is separated by clathration is a xylene, an ethyl toluene, a cymene, a diethylbenzene, a chlorotoluene, a dichlorobenzene, a toluidine, a nitrotoluene, a methylanisole or a cresol.

6. A method according to claim 5, in which the hydrocarbon which is separated by clathration is p-xylene.

7. A method according to claim 2, in which the mixture is treated with a host compound and said host compound and mixture are disposed in separate phases.

8. A method according to claim 2, in which the host compound is conditioned prior to use by formation of an adduct with the guest hydrocarbon which is to be separated from the mixture and by subsequent removal of the guest hydrocarbon therefrom.

9. A method according to claim 6 wherein said mixture comprises p-xylene and in said host compound Ar¹, Ar², Ar³ and Ar⁴ are phenyl, X and Y are P=Se and R is ethylene.

10. A method according to claim 1 in which the mixture further comprises o-xylene, m-xylene or ethylbenzene.

11. A method according to claim 1, in which each of Ar¹, Ar², Ar³ and Ar⁴ is substituted or unsubstituted aryl.

12. A method according to claim 1, in which R is methylene, ethylene or trimethylene.

13. A method according to claim 1, in which each of X and Y is identical with or different from the other and is P=Se or P=S.

14. A method according to claim 1, in which each of Ar¹, A², A³ and Ar⁴ is phenyl, X and Y are each P=Se and R is ethylene.

* * * * *